United States Patent
Forstinger et al.

(10) Patent No.: US 9,527,789 B2
(45) Date of Patent: Dec. 27, 2016

(54) METHOD FOR THE PREPARATION OF PHENOLS

(71) Applicant: WEYLCHEM FRANKFURT GMBH, Frankfurt Griesheim (DE)

(72) Inventors: Klaus Forstinger, Babenhausen (DE); Reinhard Schwesinger, Merzhausen (DE); Andreas Maier, Eppstein (DE)

(73) Assignee: WEYLCHEM FRANKFURT GMBH, Frankfurt Griesheim (DE)

( * ) Notice: Subject to any disclaimer, the term of this patent is extended or adjusted under 35 U.S.C. 154(b) by 0 days.

(21) Appl. No.: 14/907,671

(22) PCT Filed: Jul. 25, 2014

(86) PCT No.: PCT/EP2014/002033
§ 371 (c)(1),
(2) Date: Jan. 26, 2016

(87) PCT Pub. No.: WO2015/014464
PCT Pub. Date: Feb. 5, 2015

(65) Prior Publication Data
US 2016/0185695 A1    Jun. 30, 2016

(30) Foreign Application Priority Data

Jul. 27, 2013  (EP) .................. 13003758

(51) Int. Cl.
C07C 37/00    (2006.01)
C07C 37/045   (2006.01)
C07C 51/367   (2006.01)
C07C 51/00    (2006.01)

(52) U.S. Cl.
CPC ............. *C07C 37/00* (2013.01); *C07C 37/045* (2013.01); *C07C 51/00* (2013.01); *C07C 51/367* (2013.01)

(58) Field of Classification Search
None
See application file for complete search history.

(56) References Cited

U.S. PATENT DOCUMENTS

| 1,910,679 A | 5/1933 | Crawford et al. |
| 3,914,325 A | 10/1975 | Gavin et al. |
| 5,416,235 A | 5/1995 | Gilbert et al. |

FOREIGN PATENT DOCUMENTS

| CN | 102199073 A | 9/2011 |
| CN | 102746122 A | 10/2012 |
| DE | 24 26 994 A1 | 1/1975 |

OTHER PUBLICATIONS

International Search Report, PCT/EP2014/002033, Oct. 20, 2014, 2 pgs.
Ullmann's Encyclopedia of Industrial Chemistry, 7th, Completely Revised Edition (2011), vol. 11, p. 279.

*Primary Examiner* — Sudhakar Katakam
*Assistant Examiner* — Jennifer C Sawyer
(74) *Attorney, Agent, or Firm* — Paul D. Strain, Esq.; Strain & Strain PLLC

(57) ABSTRACT

The present invention relates to a method for the preparation of phenols, in which an aryldiazonium salt, which is prepared by the diazotisation of a corresponding aromatic, primary amine, is decomposed by heating in a mixture containing hot water, a mineral acid and an organic solvent, wherein the organic solvent contains a ketone of formula (I) $R^1C(O)R^2$

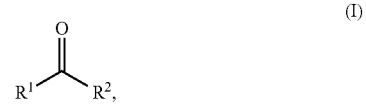

(I)

in which $R^1$ and $R^2$ independently stand for ($C_1$-$C_5$)-alkyl and $R^1$ and $R^2$ together have at least four carbon atoms, wherein the aromatic primary amine is aniline or a substituted aniline, which contains at least one further substituent which is selected from: alkyl, alkenyl, alkynyl, halogen, haloalkyl, cycloalkyl, heteroaryl, carboxyl, cyan, alkoxyl and ester, and wherein substantially no copper salts are contained in the mixture.

20 Claims, No Drawings

METHOD FOR THE PREPARATION OF PHENOLS

CROSS-REFERENCE TO RELATED PATENT APPLICATIONS

This application is a National Stage of International Application No. PCT/EP2014/002033, filed Jul. 25, 2014, which is based upon and claims the benefit of priority from prior European Patent Application No. 13003758.3, filed Jul. 27, 2013, the entire contents of all of which are incorporated herein by reference in their entirety.

The present invention relates to a method for the preparation of phenols from aromatic amines.

It is known that phenols can be prepared by thermal decomposition of diazonium salts which result from the diazotisation of aromatic amino compounds by means of nitrous acid in a cold environment. According to "Ullmann's Encyclopedia of Industrial Chemistry" (7th Completely Revised Edition, vol. 11, p. 279) the diazotisation and the thermal decomposition are best implemented in a sulphuric acid solution. The problem exists, however, that in the case of the simplest methods such as heating the diazonium salts to up to 80-100° C., the obtained product has a low purity. An increase of the yield and selectivity can sometimes be achieved by the removal of the formed phenol from the reaction mixture by means of expensive, simultaneous steam distillation (see, for example, DE 2 426 994 A1) or by dissolving the resulting phenol in xylene as an organic solvent.

A method for the preparation of phenols is known from U.S. Pat. No. 1,910,679, in which the thermal decomposition of corresponding diazonium salts in an aqueous acid solution is implemented in the presence of an organic solvent, whereby anisole, xylene or chlorobenzene are used as organic solvents. However, the yield in this method is not satisfactory.

U.S. Pat. No. 5,416,235 A and CN 102746122 A describe methods to convert aromatic amines into phenols by diazotisation and subsequent thermal decomposition in the presence of a solvent as well as of copper salts. In the examples, ethyl acetate or butyl acetate or methyl isobutyl ketone are used as solvents.

According to CN 102199073 A, 4,4'-dihydroxydiphenyl-methane can be obtained by diazotisation and thermal decomposition of 4,4'-diaminodiphenylmethane if the heating occurs in water and a solvent which is not miscible with water.

The object of the invention consists in providing a method for the preparation of phenols, using which a higher selectivity and yield of phenols can be achieved in the preparation thereof from corresponding aromatic primary amines using hydroxydediazotation.

Surprisingly, it has now been found that an increase of selectivity and yield can be achieved by using aliphatic ketones as solvents in hydroxydediazotation. These ketones are substantially poorly miscible with an aqueous medium, in that a corresponding diazo compound undergoes a decomposition.

The subject matter of the present invention is therefore a method for the preparation of phenols, in which an aryldi-azonium salt, which is prepared by the diazotisation of a corresponding aromatic primary amine, selected from aniline and substituted aniline which contains at least one further substituent which is selected from: alkyl, alkenyl, alkynyl, halogen, haloalkyl, cycloalkyl, heteroaryl, carboxyl, cyanide, alkoxyl and ester, is converted to phenol by heating in a mixture containing hot water and a mineral acid as well as an organic solvent, wherein the organic solvent contains a ketone of formula (I) $R^1C(O)R^2$

(I)

in which $R^1$ and $R^2$ independently stand for $(C_1-C_5)$-Alkyl and $R^1$ and $R^2$ together have at least four carbon atoms and wherein the solution contains substantially no copper salts during the conversion to phenol.

In the method according to the invention, a very high selectivity is surprisingly obtained in comparison to methods in which either no organic solvent or organic solvents such as xylene, chlorobenzene, toluene, methyl tert-butyl ether (MTBE), butyl acetate, etc. are used. Furthermore, a higher yield can be achieved using the method according to the invention.

In a preferred embodiment of the method according to the invention, $R^1$ and $R^2$ independently can have the following meaning in the compound of formula (I): methyl, ethyl, n-propyl, isopropyl, n-butyl, isobutyl, tert-butyl, n-pentyl, isopentyl and ten' pentyl. The compounds are preferred in which $R^1$ stands for methyl or ethyl and $R^2$ stands for ethyl or isobutyl. In particular, the compounds of formula (I) are preferred in which $R^1$ stands for methyl and $R^2$ stands for isobutyl (methyl isobutyl ketone) or $R^1$ and $R^2$ stand for ethyl (3-pentanone). Methyl isobutyl ketone is particularly preferred as a compound of formula (I).

The diazotisation reaction is implemented in a known manner (see, for example "Ullmann's Encyclopedia of Industrial Chemistry", 7th Completely Revised Edition, vol. 11, p. 279). The aromatic amine is usually diazotised in an aqueous medium in the presence of a mineral acid at a temperature from approximately −5 to approximately 50° C., preferably from approximately 0 to approximately 20° C., in the presence of a reagent suitable for diazotisation, preferably in the presence of nitrous acid.

The amines used comprise aniline and substituted anilines which contain at least one further substituent, which is selected from: alkyl, alkenyl, alkynyl, halogen, haloalkyl, cycloalkyl, heteroaryl, carboxyl, cyanide, alkoxyl and ester. The following groups are preferred: $(C_1-C_6)$-alkyl, $(C_2-C_6)$-alkenyl, $(C_2-C_6)$-alkynyl, fluorine, chlorine, bromine, iodine, $(C_1-C_3)$-haloalkyl, $(C_3-C_6)$-cycloalkyl, heteroaryl, carboxyl and ester. Primary aromatic amines which include methyl, ethyl, fluoro, chloro, bromo, iodo and/or carboxyl groups are particularly preferred.

The diazotisation agent is used in the method according to the invention generally in a stoichiometric quantity or a small excess. A molar ratio of diazotisation agent to aromatic amine of approximately 1:1 to approximately 1.5:1, preferably of approximately 1:1 to approximately 1.1:1, is suitable.

For example, alkaline nitrites such as sodium or potassium nitrite, dinitrogen trioxide and nitrous acid, nitrosyl halides such as nitrosyl chloride or bromide, and other nitrosyl salts such as nitrosyl perchlorate, nitrosyl tetrafluoroborate or nitrosyl sulphate can be used as diazotisation agents. Sodium nitrite, potassium nitrite, dinitrogen trioxide or nitrous acid are preferred, wherein sodium nitrite is particularly preferred.

The mineral acid used in the diazotisation reaction preferably has a concentration of approximately 20 to approximately 98%. A concentration of approximately 20 to approximately 50% or from approximately 95 to approximately 97% is particularly preferred. In a preferred embodiment of the invention, sulphuric acid, phosphoric acid, HCl or mixtures thereof can be used as a mineral acid during the diazotisation reaction. Sulphuric acid is particularly preferred.

The formed diazonium salt is generally decomposed (thermal decomposition) at a temperature of approximately 70 to approximately 120° C., preferably approximately 80 to approximately 100° C. The mixture containing the diazonium salt is preferably slowly dosed into a mixture of a solvent of general formula (I), hot water and a mineral acid during the decomposition. This solution contains substantially no copper salts, i.e. no copper salts (or copper) are added. Very low quantities of copper salts which could be present as impurities in the used substances do not interfere.

Typically, a proportion of the organic solvent to the aqueous mineral acids from approximately 1:100 to approximately 100:1, preferably from 1:25 to approximately 25:1, is suitable. The concentration of the mineral acid used during decomposition can lie in the range from approximately 10 to approximately 98%, preferably approximately 20 to approximately 96%.

In a preferred embodiment of the invention, sulphuric acid or a mixture of sulphuric acid and phosphoric acid is used as a mineral acid in the hydroxydediazotation. Sulphuric acid is particularly preferred.

The invention is explained by means of the following examples, without, however, being restricted to the specifically described embodiments. Insofar as nothing different is specified or must result differently from the context, percentage specifications refer to the weight, in the case of doubt to the total weight of the mixture.

The invention also relates to all combinations of preferred embodiments, insofar as these are not mutually exclusive. The specifications "approximately" or "approx." in connection with a number specification means that at least values at 10% higher or lower or values at 5% higher or lower and in any case values at 1% higher or lower are included.

Example 1

500 mL 24% sulphuric acid was introduced into a stirred flask with thermometer, stirrer and dropping funnel. 68 g anthranilic acid was added to this. This initial mixture was diazotised at 0° C. to 3° C. with 87.8 g 40% sodium nitrite solution. The diazonium salt solution was then dosed into a mixture of 25mL 24% sulphuric acid and 500mL methyl isobutyl ketone at 98° C. while stirring well. After approx. 30 min. further reaction at 98° C., a phase separation was carried out after cooling of the emulsion to approx. 85° C. The organic phase was extracted with a mixture of 750 mL water and 54 g 50% sodium hydroxide. After repeated phase separation, the target product (2-hydroxybenzoic acid) was precipitated by acidification with hydrochloric acid (pH<1.5) from the lower aqueous phase. The isolation of the end product occurred by filtration. After washing until a neutral pH value of the washing water and drying of the filter cake, 64.1 g 2-hydroxybenzoic acid was obtained with a content of 99.6% AA (according to HPLC). This corresponds to a yield of: 93.5%. The selectivity after thermal decomposition amounted to: 97.7% AA (determined by means of HPLC).

Comparative Example 2

The input volumes and the implementation of the synthesis were the same as in Example 1. However, xylene was used as an organic solvent. Resulting weight product: 55.8 g Content: 97.3% AA (HPLC) Yield: 79.3%. Selectivity after thermal decomposition: 94.2% AA (HPLC).

Example 3

700 mL 22% sulphuric acid was introduced into a stirred flask with thermometer, stirrer and dropping funnel. 70.8 g 5-chloro-2-methylaniline was added to this. After heating to 90° C. and subsequent cooling to 10° C.-12° C., the obtained suspension was diazotised with 88.4 g 40% sodium nitrite solution. The diazonium salt solution was then dosed into a mixture of 200 mL methyl isobutyl ketone and 2 g 96% sulphuric acid at approx. 85-90° C. and stirring well. After approx. 30 min. further reaction at 85-90° C., a phase separation was carried out after cooling of the emulsion to approx. 70° C. The organic phase was not processed (distilled) further. The selectivity was determined by means of GC analysis. The selectivity after thermal decomposition amounted to: 99.4% AA (GC).

Comparative Example 4

The input volumes and the implementation of the synthesis were the same as in Example 3. However, xylene was used as an organic solvent (heating temperature approx. 90° C.). The selectivity after thermal decomposition amounted to: 94.1% AA (GC).

Example 5

700mL 22% sulphuric acid was introduced into a stirred flask with thermometer, stirrer and dropping funnel. 70.8 g 3-chloro-2-methylaniline was added to this. The present suspension was diazotised with 88.4 g 40% sodium nitrite solution after heating up to approx. 90° C. and subsequent cooling to 10° C.-12° C. The diazonium salt mixture was then dosed into a mixture of 200 mL methyl isobutyl ketone and 2 g 96% sulphuric acid at approx. 90° C. and stirring well. After approx. 15 min. further reaction at 90° C., a phase separation was carried out after cooling of the emulsion to approx. 70° C. The organic phase was washed once again with 50 mL water. The selectivity after thermal decomposition amounted to: 99.1% AA (GC). The organic phase was then distilled. 66.9 g 3-chloro-2-methylphenol was obtained. Distillation residue: 2.3 g. The content of the target product amounted to: 99.2% AA (GC). This corresponds to a yield of 93.1%.

Example 6

The input volumes and the implementation of the synthesis were the same as in Example 5. However, 3-pentanone was used as an organic solvent. The selectivity after thermal decomposition amounted to: 96.9% AA (GC).

Comparative Example 7

The input volumes and the implementation of the synthesis were the same as in Example 5. However, toluene was used as an organic solvent. The selectivity after thermal decomposition amounted to: 83.0% AA (GC). End product (distilled): 58.7 g. Distillation residue: 14.8 g. The content of the target product amounted to: 97.1% AA (GC). This corresponds to a yield of 80%.

Example 8

375 mL 34% sulphuric acid was introduced into a stirred flask with thermometer, stirrer and dropping funnel. 60 g 3,4-dimethylaniline was added to this. The present suspension was diazotised with 85.5 g 40% sodium nitrite solution after heating up to approx. 75° C. and subsequent cooling to 0° C.-3° C. The diazonium salt solution was then dosed into a mixture of 50 mL methyl isobutyl ketone and 120 mL 50% sulphuric acid at approx. 85° C. and stirring well. After approx. 30 min. further reaction at 85° C., a phase separation was carried out after cooling of the emulsion to approx. 35° C. The organic phase was not processed (distilled) further. The selectivity was determined by means of GC analysis. The selectivity after thermal decomposition amounted to: 97.2% AA (GC). After removal of the solvent, the yield of product amounted to 94.5%.

Comparative Example 9

The input volumes and the implementation of the synthesis were the same as in Example 8. However, xylene was used as an organic solvent. The selectivity after thermal decomposition amounted to: 93.1% AA (GC). After removal of the solvent, the yield of 3,4-dimethylphenol amounted to 80.1%.

Comparative Example 10

The input volumes and the implementation of the synthesis were the same as in Example 8. However, chlorobenzene was used as an organic solvent. The selectivity after thermal decomposition amounted to: 94.2% AA (GC). After removal of the solvent, the yield of 3,4-dimethylphenol amounted to 80.0%.

Comparative Example 11

The input volumes and the implementation of the synthesis were the same as in Example 8. No organic solvent was used during thermal decomposition. The selectivity after thermal decomposition amounted to: 82.8% AA (GC). After removal of the solvent, the yield of 3,4-dimethylphenol amounted to 59.2%.

Comparative Example 12

The use quantities and the implementation of the synthesis were the same as in Example 8. However, cyclohexanone was used as an organic solvent. The selectivity after thermal decomposition amounted to: 80.2% AA (GC). The yield of 3,4-dimethylphenol amounted to 70.2% after distillation.

Comparative Example 13

The input volumes and the implementation of the synthesis were the same as in Example 8. However, methylcyclohexane was used as an organic solvent. The selectivity after thermal decomposition amounted to: 76.6% AA (GC). After removal of the solvent, the yield of 3,4-dimethylphenol amounted to 75.2%.

Comparative Example 14

The input volumes and the implementation of the synthesis were the same as in Example 8. However, ethyl acetate was used as an organic solvent. The selectivity after thermal decomposition amounted to: 83.9% AA (GC).

As the exemplary embodiments show, using the method according to the invention, a clear increase of the selectivity and yield in comparison both to the organic solvents previously used in prior art such as xylene or chlorobenzene, as well as to solvents such as toluene, cyclohexanone or methylcyclohexane can be achieved.

Comparison With CN 102746122

According to Example 1 in CN 102746122 27.8 g p-aminophenol was added to 408 g 15% sulphuric acid in a 1l reactor and mixed. 48 g 40% sodium nitrite solution was added in drops within 1 h at 0° C.-5° C. Complete conversion to diazonium salt. Excess sodium nitrite was decomposed by means of amidosulphonic acid. The obtained mixture was added in drops into a stirred 2l reactor at 88 to 90° C. within 1 h, into which reactor 300 ml water, 42.5 g basic copper carbonate, 143.5 g copper sulphate pentahydrate in water and 200 g n-butyl acetate or 200 g methyl isobutyl ketone or 200 g ethyl acetate (deviating conversion temperature 70° C.-73° C.) were introduced. After 3 hours of stirring and cooling to 20° C. overnight, the solvent phase was separated, the aqueous phase was extracted twice with 100 g each of the used solvent and the selectivity was determined by HPLC. The test of a conversion in xylene was not successful.

The following Table 1 shows the results.

TABLE 1

| Solvent | Selectivity |
| --- | --- |
| MIBK | 76.6% |
| Butyl acetate | 74.9% |
| Ethyl acetate | 82.0% |

It is recognised that the selectivities achieved with MIBK are comparable with n-butyl acetate and poorer than with ethyl acetate. Furthermore it can be determined that despite the use of high quantities of copper, the selectivities are still not satisfactory. The handling of the large quantities of copper salts is difficult anyway, even if these can be processed as described in CN 102746122 and can be returned into the process.

The invention claimed is:
1. A method for the preparation of phenols in which an aryldiazonium salt, which is prepared by the diazotisation of a corresponding aromatic primary amine, is decomposed by heating in a mixture containing hot water, a mineral acid and an organic solvent, wherein, the organic solvent contains a ketone of formula (I)
$R^1C(O)R^2$

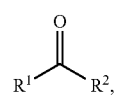

(I)

in which $R^1$ and $R^2$ independently stand for $(C_1-C_5)$-alkyl and $R^1$ and $R^2$ together have at least four carbon atoms, wherein the aromatic primary amine is aniline or a substituted aniline which contains at least one further substituent which is selected from the group consisting of alkyl, alkenyl, alkynyl, halogen, haloalkyl, cycloalkyl, heteroaryl, carboxyl, cyanide, alkoxyl and ester, and wherein substantially no copper salts are contained in the mixture containing hot water, a mineral acid and an organic solvent.

2. The method according to claim 1, wherein the aniline contains at least one further substituent, which is selected from the group consisting of $(C_1-C_6)$-alkyl, $(C_2-C_6)$-alkenyl, $(C_2-C_6)$-alkynyl, fluorine, chlorine, bromine, iodine, $(C_1-C_3)$-haloalkyl, $(C_3-C_6)$-cycloalkyl, heteroaryl, carboxyl and ester.

3. The method according to claim 2, wherein the further substituent is selected from the group consisting of methyl, ethyl, fluoro, chloro, bromo, iodo, carboxyl groups and two or more thereof.

4. The method according to claim 1, wherein $R^1$ and $R^2$ are independently selected from the group consisting of methyl, ethyl, n-propyl, isopropyl, n-butyl, isobutyl, tent-butyl, n-pentyl, isopentyl, and tent-pentyl.

5. The method according to claim 4, wherein $R^1$ stands for methyl or ethyl and $R^2$ stands for ethyl or isobutyl.

6. The method according to claim 5, wherein methyl isobutyl ketone or 3-pentanone is used as the ketone of formula (I).

7. The method according to claim 1, wherein the concentration of the mineral acid amounts from approximately 10 to approximately 98%.

8. The method according to claim 1, wherein the ratio of amount of the organic solvent of formula (I) to the aqueous solution of the mineral acid amounts to approximately 1:100 to approximately 100:1.

9. The method according to claim 1, wherein sulphuric acid or phosphoric acid is used as the mineral acid.

10. The method according to claim 1, wherein the aryldiazonium salt is decomposed at a temperature of approximately 70 to approximately 120° C.

11. The method according to claim 5, wherein $R^1$ stands for methyl and $R^2$ stands for isobutyl or $R^1$ and $R^2$ stand for ethyl.

12. The method according to claim 6, wherein methyl isobutyl ketone is used as the ketone of formula (I).

13. The method according to claim 7, wherein the concentration of the mineral acid amounts from approximately 20 to approximately 50%.

14. The method according to claim 7, wherein the concentration of the mineral acid amounts from approximately 95 to approximately 97%.

15. The method according to claim 8, wherein the ratio of amount of the organic solvent of formula (I) to the aqueous solution of the mineral acid amounts to approximately 1:25 to approximately 25:1.

16. The method according to claim 9, wherein sulphuric acid is used as the mineral acid.

17. The method according to claim 10, wherein the aryldiazonium salt is decomposed at a temperature of approximately 80 to approximately 110° C.

18. The method according to claim 3, wherein $R^1$ and $R^2$ are independently selected from the group consisting of methyl, ethyl, n-propyl, isopropyl, n-butyl, isobutyl, tert-butyl, n-pentyl, isopentyl, and tert-pentyl.

19. The method according to claim 3, wherein methyl isobutyl ketone or 3-pentanone is used as the ketone of formula (I).

20. The method according to claim 7, wherein sulphuric acid is used as the mineral acid.

\* \* \* \* \*